United States Patent [19]

Houser

[11] Patent Number: 5,053,118
[45] Date of Patent: Oct. 1, 1991

[54] BITUMEN EXTRACTION FROM ASPHALT PAVEMENTS

[76] Inventor: Thomas Houser, Department of Chemistry, Western Michigan University, Kalamazoo, Mich. 49008-3842

[21] Appl. No.: 546,887

[22] Filed: Jul. 2, 1990

[51] Int. Cl.$^5$ ................................. C10G 21/00
[52] U.S. Cl. .................... 208/45; 208/309; 208/428; 106/273.1
[58] Field of Search .............. 208/45, 304, 428; 106/273.1

[56] References Cited

U.S. PATENT DOCUMENTS

| | | | |
|---|---|---|---|
| 2,383,363 | 8/1945 | Bathchelder | 208/45 |
| 2,421,421 | 5/1944 | Hoiberg | 106/273.1 |
| 2,940,920 | 6/1960 | Garwin | 208/45 |
| 2,967,818 | 1/1961 | Garwin | 208/45 |
| 3,971,666 | 7/1976 | Mendenhall | 106/273.1 |
| 4,021,393 | 5/1977 | McDonald | 106/273.1 |
| 4,025,057 | 5/1977 | Shearer | 106/273.1 |
| 4,279,660 | 7/1981 | Kamo et al. | 208/45 |
| 4,305,814 | 12/1981 | Leonard | 208/309 |
| 4,341,619 | 7/1982 | Poska | 208/11 LE |
| 4,354,928 | 10/1982 | Audeh et al. | 208/309 |
| 4,376,693 | 3/1983 | Warzel | 208/11 LE |
| 4,482,453 | 11/1984 | Coombs et al. | 208/309 |
| 4,502,944 | 3/1985 | Nelson | 208/45 |
| 4,588,476 | 5/1986 | Warzel | 196/14.52 |
| 4,663,028 | 5/1987 | Ditman | 208/309 |
| 4,675,101 | 6/1987 | Warzinski | 208/309 |
| 4,695,372 | 9/1987 | Warzinski | 208/309 |
| 4,737,267 | 8/1988 | Pao et al. | 208/432 |
| 4,755,278 | 7/1988 | Baumgartner | 208/45 |
| 4,784,753 | 11/1988 | Hotier et al. | 208/309 |

FOREIGN PATENT DOCUMENTS 1118423  2/1983  Japan .................. 106/273.1

OTHER PUBLICATIONS

ASTM D2172-81, Quantative Extraction of Bitumen from Bituminous Paving Mixtures.
MTM 301-76 (Michigan), Test for Characteristics of Bituminous Metal After Mixing.
ASTM D 1856-79, Recovery of Asphalt from Solution by Abson Method.
PTM 702-86 (Pennsylvania), Method of Test for Quantitative Extraction of Bitumen from Bituminous Paving Mixtures.
AASHTO T164-86, Quantitative Extraction of Bitumen from Bituminous Paving Mixtures.
Gilson Vacuum Extractor Model HM-8, Operating Instructions (Gilson Co., Inc., Worthington, Ohio).
Model AP-520, The Vacuum Extractor, Operation and Service Lustrations (Soiltest, Inc., Evanston, Ill.).
Williams, D. F., *Chem. Eng. Sci.*, 36:1769–1788 (1981).
Gangoli, N & Thodos, G., *Ind. Eng. Chem., Prod. Res. Dev.*, 16(3):208–216 (1977).

Primary Examiner—Helane E. Myers
Attorney, Agent, or Firm—Christopher John Rudy

[57] ABSTRACT

The composition of asphalt pavements can be determined through bitument extraction, employing an alicyclic hydrocarbon as extractant under subcritical conditions. For example, cyclohexane is so employed in conjunction with an apparatus hereof.

10 Claims, 4 Drawing Sheets

BITUMEN EXTRACTION FROM ASPHALT PAVEMENTS

FIELD

This invention concerns bitumen extraction of an asphalt pavement, useful in the determination of the composition of the pavement, with a procedure and apparatus therefor.

BACKGROUND

Various organizations to include the various departments of transportation and the like, for example, throughout the U.S.A., Canada, and so forth, perform numerous asphalt extraction tests yearly for quality control and performance evaluation. The most critical step in the known test procedures is the quantitative extraction of bitumen from the asphalt paving mixtures. Other determinations useful in evaluating these mixtures include the particle size distribution of the aggregate after extraction and the hardness of the extracted bitumen after solvent removal (penetration test)

The procedure used currently by the Michigan Department of Transportation (MDOT), based on ASTM D 2172-81, involves soaking the paving mixture in a solvent at ambient temperatures, followed by separation of the solvent-bitumen mixture from the aggregate by a complex procedure employing a centrifuge and repeated solvent washings The solvents that have been found to be effective and are extensively used are trichloroethylene (TCE), 1,1,1-trichloroethane (111-TCE), and methylene chloride (MeCl2). Unfortunately, because of their chlorine content these solvents present a serious problem for hazardous waste disposal. In order to minimize this problem, the MDOT eliminated TCE from use for their field extractions, although it is still being used in their Lansing laboratory. A commercial solvent, BIOACT-DG-1, which is primarily limonene, a terpine hydrocarbon, has been substituted for TCE in the field testing because it does not have the hazardous waste disposal problem as does TCE, nor does it appear to present a significant health hazard to exposed personnel, even though some workers have experienced some irritation due to its odor. In addition, BIOACT-DG-1 can be used with essentially the same equipment as is used with TCE. However, BIOACT-DG-1 presents several disadvantages when compared with the commonly used solvents for such extractions, among which include the following: (1) It is significantly more expensive. (2) It extracts the bitumen more slowly. (3) Its high boiling point does not allow for its separation from the extract so that a penetration test may be performed (4) It apparently undergoes a phase separation when stored at low temperatures such as in the winter, giving a solvent with inconsistent properties.

The Vermont Agency of Transportation has used xylene in place of TCE, and although it performs satisfactorily as a solvent, it is reported to present a serious health hazard to personnel. Preliminary tests were conducted to determine the suitability of substituting BIOACT-DG-1 for xylene, which, again, indicated that BIOACT-DG-1 could function as an extractant of the bitumen, but it took twice as long to do this as did xylene and was significantly more expensive It should be noted that solvents with higher boiling points than TCE, such as xylene or toluene, would be very difficult to separate from the extracted bitumen without excessive heating, thus limiting penetration testing and so forth.

The Pennsylvania Department of Transportation (PDT) employs a method for the quantitative extraction of bitumen from bituminous paving mixtures that is a modification of AASHTO T-164, a method similar to ASTM D 2172-81. Extraction of the paving mixture in the PDT method is conducted with 111-TCE or with toluene.

Alternate methods for bitumen extraction involving solvent reflux or vacuum filtration also have been developed for use with the chlorinated solvents. However, these do not avoid or overcome the mentioned problems encountered by use of these solvents.

An apparatus useful in such tests as the ASTM D 2172-81 and AASHTO T-164 is the Gilson Vacuum Extractor Model HM-8 (Gilson Co., Inc., Worthington, OH).

An apparatus useful in ASTM D 2172-81 testings is the Soiltest Vacuum Extractor Model AP-520 (Soiltest, Inc., Evanston, Ill.).

OBJECTS

An object hereof was the development of a bitumen extraction procedure that is competitive in both cost and time consumption with those currently in use, that is simple in nature so that it can be performed by non-professional staff, and that would not employ chlorinated or aromatic solvents. An ancillary object hereof was the development of apparatus which can be employed in the procedure. Other objects hereof were extant as well.

Achievement of such objects would fulfill lacks and long felt needs in the pertinent art.

COMPARATIVE APPROACH

Initially in attempts to satisfy the objects hereof an approach was the investigation of supercritical fluid extraction (SFE) since fluids at these conditions have greatly increased solubility for many non-volatile materials, with increases of several orders of magnitude being common. See e.g., *Williams, Chem. Enq. Sci.* 36:1769 (1981); Gangoli & Thodos, *Ind. Enq. Chem.: Prod. Res. Dev.* 16(3):208 (1977). Thus, solvents which are not effective solvents at or near ambient conditions for bitumen extraction may be effective at supercritical conditions However, SFE was found to be comparatively impractical. The large size of the pavement samples necessary to be representative of the production mix required heating times too long for solvents effective in the present invention such as cyclopentane and cyclohexane In addition, the high, 280 degree C., critical temperature of cyclohexane, for example, created problems in VITON O-rings in an apparatus of the present invention employed under these SFE conditions. Furthermore, a metal screen in an apparatus of the present invention, which had the smallest holes readily available, 10 microns, still let fines through in SFE, and filter paper employed in lieu thereof showed charring under these SFE conditions. Other problems attend SFE use. For example, solvents with lower critical temperatures were found to be not effective.

OTHER INFORMATION

Poska, U.S. Pat. No. 4,341,619 (July 27, 1982), discloses supercritical tar sand extraction. The supercritical tar sand extraction is carried out by countercurrent flow of the tar sand and solvent and preferably employs a purge gas. Numerous solvents or extractants are disclosed to be employable in that invention. See e.g., columns 3–4.

Warzel, U.S. Pat. No. 4,376,693 (Mar. 15, 1983), discloses solid liquid extraction. In nature and gist, that invention is a process for replacing a solution obtained, for instance, by exposing oil shale particles to the action of a solvent under supercritical conditions, by a solvent. The solid/solution mixture is extracted in a multitude of cross flow extractions such as to gradually replace the solution, e.g., a bitumen solution, by the solvent, e.g., toluene. An apparatus useful therefor is also disclosed.

Warzel, U.S. Pat. No. 4,588,476 (May 13, 1986), discloses a solid liquid extraction apparatus. This patent is a divisional of Warzel '693

Pao et al., U.S. Pat. No. 4,737,267 (Apr. 12, 1988), discloses an oil shale processing apparatus and method. That invention relates to a process for extracting bitumen from oil shale, and more particularly, to a process and apparatus for extracting bitumen using supercritical solvent techniques. Good solvents for use therein are hydrocarbons with a normal boiling range of 80 to 200 degrees C., preferably for example, toluene. See e.g., column 4:57–68.

Garwin, U.S. Pat. No. 2,940,920 (June 14, 1960), discloses separation of asphalt-type bituminous materials. That invention relates to a method of separating an asphalt-type bituminous material into two or more fractions, more particularly employing certain hydrocarbon solvents. See e.g., column 5:10–49.

Leonard, U.S. Pat. No. 4,305,814 (Dec. 15, 1981), discloses an energy efficient process for separating hydrocarbonaceous materials into various fractions. That invention relates to a process for separating a hydrocarbon feed into various fractions employing solvents at elevate temperatures and pressures, and more particularly, to a process for recovering the solvent from the separated fractions. An exemplary solvent comprises pentane.

Audeh et al., U.S. Pat. No. 4,354,928 (Oct. 19, 1982discloses supercritical selective extraction of hydrocarbons from asphaltic petroleum oils. That invention relates to the recovery of hydrocarbon oils from petroleum residue, and more particularly, to a process for selectively extracting heavy hydrocarbons from asphalt-containing petroleum oils.

Coombs et al., U.S. Pat. No. 4,482,453 (Nov. 13, 1984), discloses a supercritical extraction process. In nature and gist, that invention discloses that the recovery of hydrocarbon values from high metals content feeds can be carried out more efficiently via supercritical extraction with recycle of a portion of the asphalt product and proper control of the use of countercurrent solvent flow to the extraction. Sundry solvents are generally useful therein, and preferred solvents are five to seven carbon paraffins and mixtures thereof. See e.g., column 3:1–19.

Nelson, U.S. Pat. No. 4,502,944 (Mar. 5, 1985), discloses fractionation of heavy hydrocarbon process material. That invention relates to a method of separating a heavy hydrocarbon process material comprising asphaltenes, resins and oils into at least three fractions, and more particularly, to such a method employing light organic solvents under elevated temperature and pressure conditions. The solvent is selected from three to eight carbon paraffinic hydrocarbons, preferably comprising pentane.

Hotier et al., U.S. Pat. No. 4,784,753 (Nov. 15, 1988), discloses a deasphalting process comprising power recovery from the stage of separating deasphalted oil from the deasphalting solvent. In summary, that invention concerns processes of the type disclosed in the Garwin, Leonard, and Nelson patents and provides a method for increasing to a maximum extent the power recovery during supercritical separation of deasphalted oil from the deasphalting solvent, which comprises at least on hydrocarbon having three to six carbons. See e.g., column 2:40–54.

INVENTION SUMMARY

The present invention provides in one aspect a procedure for bitumen extraction from an asphalt pavement sample comprising contacting the asphalt pavement sample with an alicyclic hydrocarbon solvent and under subcritical conditions at an extranormal temperature and pressure extracting bitumen from the asphalt pavement sample thereby. Another aspect hereof is an apparatus comprising a housing section having imperforate walls, which is generally divided into lower and upper housing sections about a means for filtration, the lower housing section having imperforate lower and side walls and connectable to the upper housing section having imperforate side walls, the means for filtration being generally between interior volumes of the lower and upper housing sections, and an imperforate lid, useful for making a sealable bomb.

The present invention is useful in determining the composition of an asphalt pavement sample.

Significantly, the procedure employs the alicyclic remarkably simple, accurate, and efficient, both in time consumption and cost. Problems associated with the use of other known solvents for bitumen extraction from an asphalt pavement sample such as the chlorinated hydrocarbons and aromatic hydrocarbons are avoided. The procedure, although typically taking slightly more time than known test methods employing the chlorinated hydrocarbons, takes less time to complete than known test methods employing BIOACT-DG-1. In addition, the apparatus is simple, avoiding the need for centrifuge apparatus and/or such accessories as an exterior high performance vacuum pump and integral and exterior vacuum conduits, valves, and so forth, and is especially adapted for use in procedural embodiments hereof. Taken as a whole, with the the procedure and apparatus hereof employed in conjunction, the present invention provides substantial cost advantages over the known art. This invention achieves many if not all of its objects Further advantages attend this invention as well.

DRAWINGS

The drawings form part of the specification hereof.

ILLUSTRATIVE DETAIL

Figure 1:
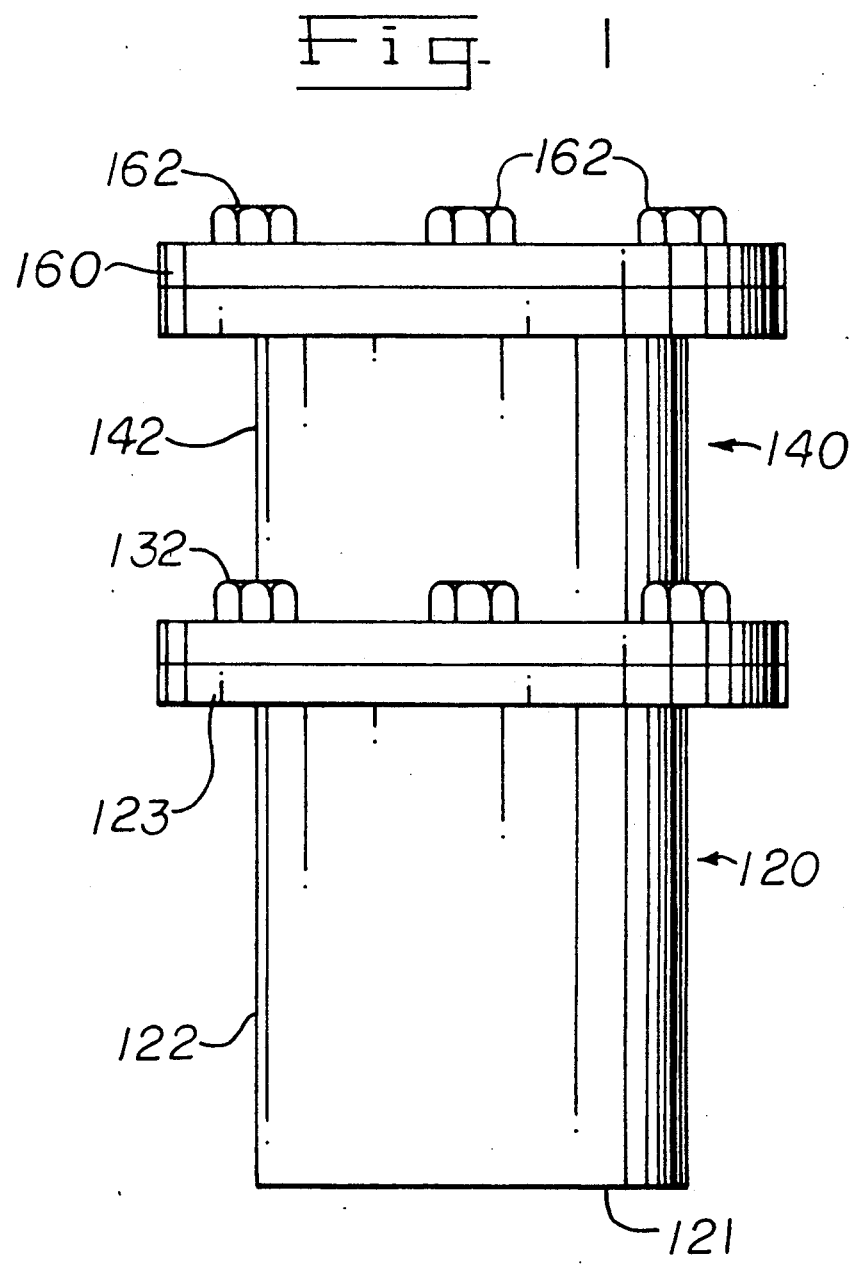
FIG. 1 (FIG. 1) is a side view of an apparatus of the present invention.
Figure 2:
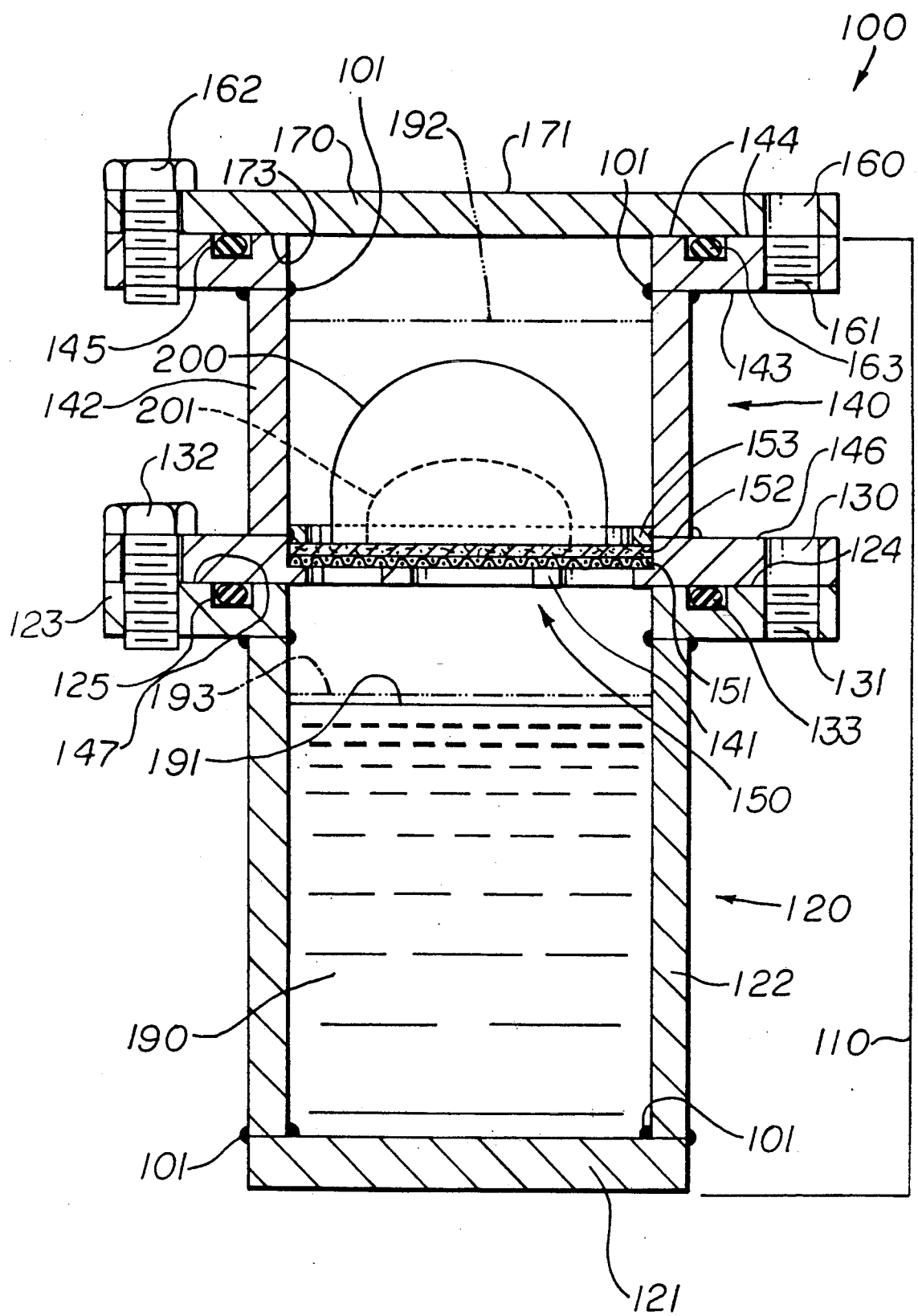
FIG. 2 (FIG. 2) is a sectional side view of the apparatus of FIG. 1.
Figure 3:
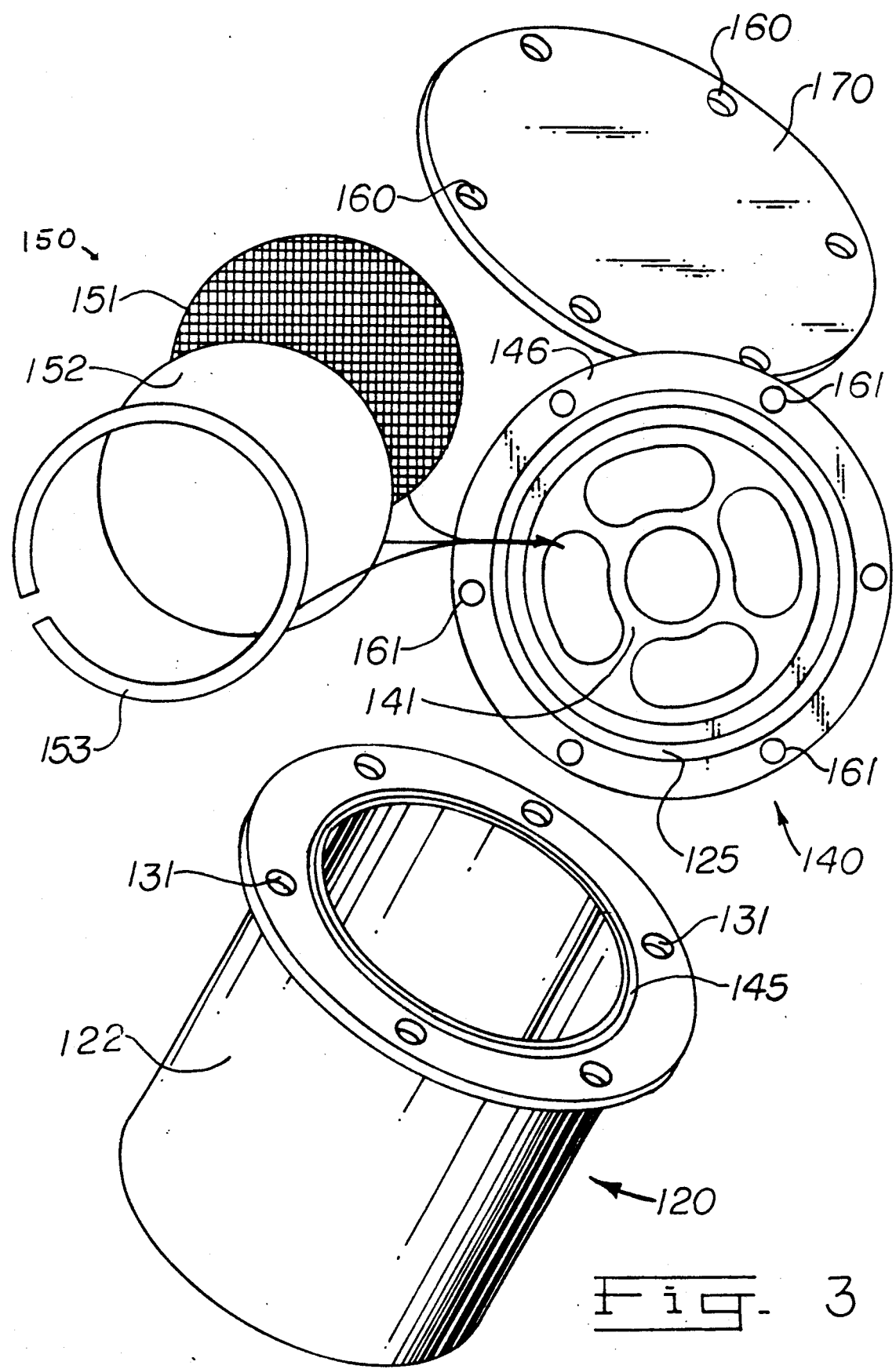
FIG. 3 (FIG. 3) is an exploded top perspective view of the apparatus otherwise as of FIG. 1.

Herein, a procedure is a method and/or process.

In the procedural practice of this invention, the asphalt pavement sample and the alicyclic hydrocarbon solvent are contacted under subcritical conditions, and an extranormal temperature and pressure are employed. Bitumen is extracted from the asphalt pavement sample.

The term, "asphalt pavement sample," herein refers to a sample taken from an asphalt paving substance, a mixture or composition, to include such paving mixtures or compositions as extant before, during, and after application as a surface for a roadway, sidewalk, parking lot, terrace, and so forth and the like. The asphalt pavement sample may be one which has been taken from an existing roadway, sidewalk, parking lot, terrace, or other such surface after its application. Preferably as generally appropriate, such an asphalt pavement sample is about from 1 to 2.5 kg in mass, depending on aggregate particle sizes. The sample may be made up of irregularly shaped chunks, grindings, crushings, and so forth and the like or may be of a regular shape such as cube or cylindrical like and so forth. In general, the asphalt pavement sample is representative of the whole asphalt paving substance and typically contains asphalt and aggregate. The asphalt is predominately made up of bitumen The term, "alicyclic hydrocarbon solvent," is an aliphatic cyclic hydrocarbon compound or mixture of such compounds which can function as an extractant of bitumen from the asphalt pavement sample and in which the aggregate is essentially insoluble. The alicyclic hydrocarbon solvent includes cycloalkanes, e.g., cyclobutane, cyclopentane, methylcyclopentane, cyclohexane, methylcyclohexane, and so forth, and cycloalkenes, e.g., cyclohexene, and so forth, typically including compounds of four to twelve carbon atoms. Preferably, the alicyclic hydrocarbon solvent is a cycloalkyl compound or mixture of such compounds. The alicyclic hydrocarbon solvent can be such a cycloalkyl compound as cyclopentane or cyclohexane. Cyclohexane is especially preferred.

Contact of the sample and solvent is made under subcritical conditions. To extract the bitumen, extranormal temperatures and pressures are employed.

The term, "extranormal temperature," herein refers to a subcritical temperature of the alicyclic hydrocarbon solvent generally above the normal boiling point of the lowest boiling component of the solvent. The extranormal temperature can be generally inclusive of a temperature value of at least about 50 percent of those temperatures within the range from the normal boiling point of the lowest boiling component of the solvent to the critical temperature of the solvent, often about from 75 to 90 percent of those temperatures within the range from the normal boiling point of the lowest boiling component of the solvent to the critical temperature of the solvent. Advantageously, the extranormal temperature is at least about 180 degrees C., preferably about from 220 to 250 degrees C.

The term, "extranormal pressure," herein refers to a pressure which is supra-atmospheric. This may include a pressure about from 5 to 50 atm, preferably about from 20 to 35 atm.

In general, times that the sample and solvent are subjected to the extranormal temperature and pressure may vary depending upon the sample, the solvent, and the extent of extraction desired. Typically, these times are about from 0.5 to 24 hours, preferably about from 1 to 5 hours. A heating phase can begin these times where the sample and solvent, typically in the apparatus hereof, are heated for a time, say, about from 0.25 to 20 hours, preferably about from 1 to 1.5 hours. This heating phase can be followed by a cool down phase where the heated sample and solvent, typically in the apparatus hereof, are cooled to more moderate temperatures such as about from the temperature of ice water to room temperature or so, advantageously gradually, say, about from 0.25 to 4 hours, preferably about from 0.75 to 1.5 hours, especially substantially step-wise as by a gradual cool down period such as initially in ambient air followed by another gradual cool down period such as in cool water, e.g., water about from 10 to 15 degrees C., with preferably, the air type cool down period being about from 0.5 to 1 hour and the water type cool down period being about from 0.25 to 0.75 hours Other heat transfer substances such as metals, ethylene and/or propylene glycol(s), and so forth and the like may be employed.

The solvent extracts and contains the bitumen, leaving the aggregate. Washing of the remaining aggregate and the apparatus employed, say, with cool to somewhat heated solvent, may be carried out, and these washings are preferably added to the original solvent for a determination of bitumen. Substantially quantitative extraction of bitumen can result.

The aggregate can be weighed after drying and/or further analyzed if desired Typically, the aggregate is weighed in a determination of the sample composition An aggregate size distribution determination can be conducted. Other analyses may be conducted.

The extract containing the bitumen can be further analyzed. For example, it can be distilled by known methods to recover the bitumen for a penetration test such as conducted by known methods. The solvent may be recycled. Other analyses may be conducted.

Preferably, the procedure is carried out with the apparatus of the invention. Decided advantages thus follow.

In general, the apparatus of the present invention is a sealable bomb. It comprises the following features:

A housing section having imperforate walls, which is generally divided into lower and upper housing sections about a means for filtration.

Lower housing section having imperforate lower and side walls.

Upper housing section having imperforate side walls.

Means for filtration generally between volumes of the lower and upper housing sections.

An imperforate lid.

Figure 5:
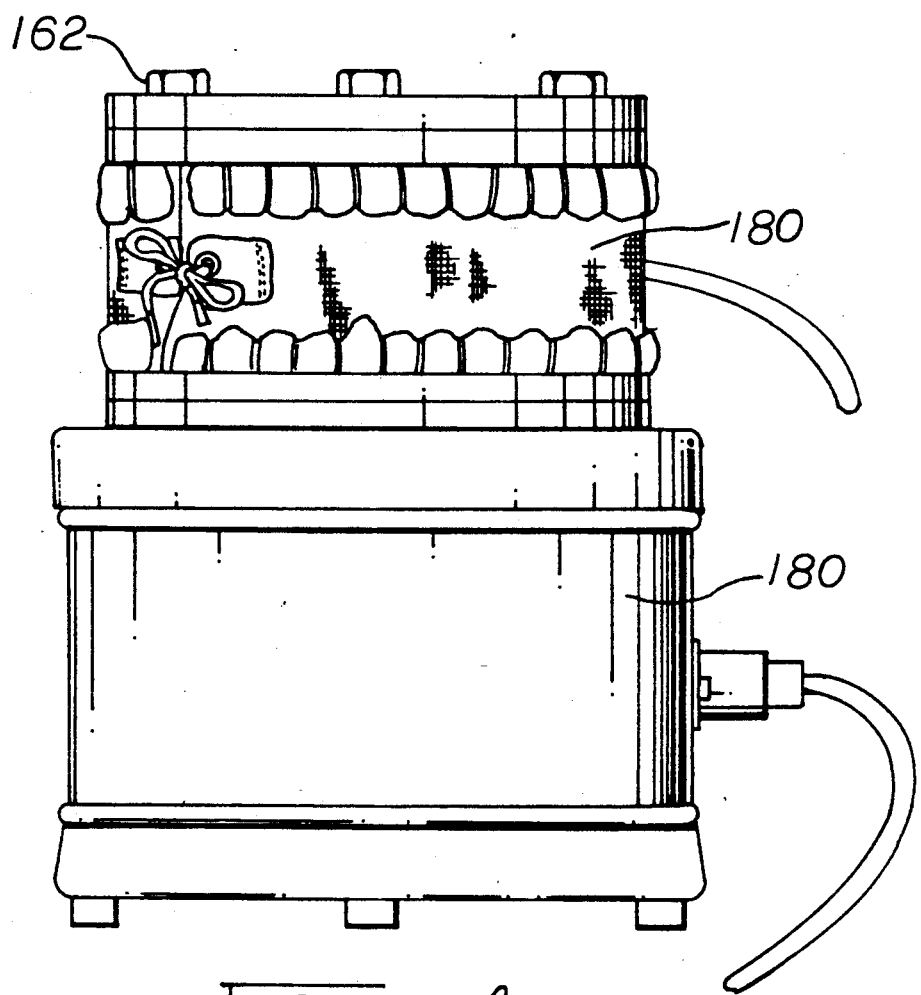
FIG. 5 (FIG. 5) is a side view of the apparatus of FIG. 1 residing in heating mantles.

In reference to the drawings, apparatus 100, made of a suitable material, preferably predominately of a stainless steel, e.g., number 316 stainless steel, is depicted. The apparatus has housing section 110 having lower housing section 120 and upper housing section 140. The lower housing section has lower wall 121, side wall 122, flange 123, mating surface 124 and groove 125. The upper housing section, having support grill 141, side wall 142, upper flange 143, upper mating surface 144, groove 145, lower flange 146 and lower mating surface 147, can connect to the lower housing section by means for fastening 130, threads 131 and bolts 132. Residing upon the support grill of the upper housing section is means for filtration 150, having filter screen 151, e.g., number 700 mesh stainless steel, filter paper 152, and retaining ring 153, e.g., of about 0.25-inch (0.635-cm) by about 0.125-inch (0.3175-cm) stainless steel, resting thereon interposited between the lower and upper housing sections for residence in the appropriate groove is O-ring 133 made of a suitable material, e.g., a fluoroelastomer copolymerized from monomeric vinylidene fluoride and hexafluoropropylene, i.e., VITON. Lid 170 has imperforate wall 171 and mating surface 173, and it can connect to the upper housing section by means for fastening 160, threads 161 and bolts 162. Interposited between the upper housing section and the lid for residence in the appropriate groove is O-ring 163, e.g., of VITON. See, FIGS. 1–4. Means for heating 180 can be external as depicted in FIG. 5, and/or the means for heating can be made integrally incorporated with the apparatus.

The apparatus is suitably dimensioned. For example, the preferred embodiment of apparatus 100 has an inside diameter for its housing 110 of about 5.3125 inches (13.5 cm). Its lower housing section 120 has a height of about 6.375 inches (16.2 cm) to define an interior volume of about 2300 cc. Its upper housing section 140 has a height of about 4.25 inches (10.8 cm) to define an interior volume of about 1450 cc. Also, the thickness of each of walls 122 & 142 is about 0.125 of an inch (0.3175 cm), of each of walls 121 & 171 is about 0.5 of an inch (0.27 cm), of each of flanges 123, 143 & 146 is about 0.4375 of an inch (1.11125 cm), and of support grill 141 is about 0.25 of an inch (0.635 cm). Grooves 125 & 145 are made to size 2-359 The apparatus may be smaller or larger, of course. For example, a smaller apparatus, analogously scaled down from the mentioned dimensions of the preferred exemplary apparatus 100, has interior volumes defined by its lower and upper housing sections of 200 cc each, and is satisfactorily operable with asphalt pavement samples including those about from 100 to 160 g.

The apparatus hereof can be made by known procedures. For example, in further reference to the drawings, welds 101 are extant from the making of apparatus 100. Polishing, cutting, routing, tapping, and so forth may precede or follow in the making of the apparatus after the welding. Casting or drop-forging and so forth may be employed In preferred practice in the procedure of the invention, the lower housing section of the apparatus is provided with a predetermined amount of the solvent 190, say, an amount that will fill about from 70 to 90 percent of the interior volume thereof to a first level 191. A predetermined amount of the sample 200 is placed upon the means for filtering, and the apparatus is sealed by the means for fastening. The apparatus is then heated by the means for heating through its lower and upper sections, leaving the lid relatively cool, causing the contents of the apparatus to heat up and the solvent in particular to expand in volume to a second level 192 in the upper housing section to immerse the sample in the hot solvent under pressure The lower housing section is then cooled causing solvent contraction to a third level 193 typically about the first level, bringing bitumen with the solvent into the lower housing section and leaving aggregate 201. See, FIG. 2. The substantially step-wise cooling as by the gradual cool down period such as initially in ambient air followed by another gradual cool down period such as in cool water is carried out. The initial air cooling prevents too large a pressure differential from developing between the sections. The lower and upper housing sections may be disconnected s that the solvent extract may be more conveniently transferred from the lower housing section to another vessel such as for distillation. Washes with ambient solvent may be carried out with vacuum filtration to complete the extraction. Remaining aggregate is dried and weighed, and the solvent may be distilled from the extract plus washings to get a direct measure of bitumen content. Recovered bitumen may be used for a penetration test.

In addition to the aforesummarized advantages, another advantage of the present invention through its subcritical condition extraction procedure employing the present apparatus is that some surfaces of the apparatus, e.g., the procedure since the solvent exists both as liquid and vapor. Plus, the heating can be accomplished much more quickly and efficiently with the means for heating such as depicted in contrast to the use of an oven such as with supercritical fluid extraction procedures for determination of the composition of asphalt pavements.

The following further illustrates the invention. Therein, percentages are by weight.

COMPARATIVE DATA

Asphalt pavement samples, per lot, were obtained and reported to have been tested in the quantitative extraction of bitumen and recovered penetration testing procedures of the MDOT. The solvent employed was TCE.

The following results were provided.

| Lot | Percent Bitumen | Recovered Penetration Value (R-Pen) |
|---|---|---|
| A | 5.6–5.8 | — |
| B | 5.5–5.6 | 165 |
| C | 5.6–5.8 | 141 |
| D | 5.6–6.0 | 108 |
| E | 6.6–6.9 | 192 |
| F | 5.5–5.6 | 165 |

EXAMPLE OF THE INVENTION

Into the lower housing section of the preferred apparatus 100, made predominately of number 316 stainless steel and having the noted larger dimensions, VITON O-rings (Ronningen-Petter, Div. Dover Resources Co., Portage, Mich.) and as part of its means for filtration grade 627-85 filter paper (Filtration Sciences Corp., Eaton-Dikeman Div., Mount Holly Park, Penn.), was charged 1780 mL of cyclohexane. A predetermined amount of an asphalt pavement sample, per the same lots as in the comparative example, was placed on top of the means for filtration. The lower and upper housing sections and the lid were bolted tightly to form a unit. The lower housing section was placed into a standard 3-L beaker sized heating mantle (Glas-Col, Terre Haute, Ind.), and the upper housing section was wrapped in a custom-made heating mantle jacket (Glas-Col, Terre Haute, Ind.) which surrounded the upper housing section.

A standard electric current of 115 V was applied to both heating mantles for 75 minutes. The solvent temperature came to 230–240 degrees C., and the pressure came to 25-30 atm. The heating mantles were removed, and the unit was allowed to cool with ambient air blowing onto the lower section for 40 minutes, followed by cooling of the unit, lower section first, in about 10-degree C. tap water for 20 minutes, with the lower section having been so water-cooled for the first 10 minutes thereof.

Following the cooling, the unit was opened, and the solvent/extract was decanted into a 4-L polyethylene beaker and set aside. The retaining ring was removed, and the aggregate was removed into a 4-L polyethylene beaker. The apparatus parts, to include the ring, screen, filter paper, upper and lower housing sections, lid and O-rings, were rinsed with ambient cyclohexane, and solids that were left on the screen and filter paper were all washed into the 4-L beaker. The aggregate washing was filtered using a Buchner funnel, and then the aggregate was repeatedly rinsed with ambient cyclohexane until the filtrate was a light straw color (4 or 5 washings). These filtrates were combined and set aside. In order to speed up the drying process, the cyclohexane washings were followed by two washings wit n-pentane (Other low boiling solvents such as diethyl ether, etc., could be used.) to remove the cyclohexane; these aggregate was transferred into a 3-L pyrex beaker.

The combined amount of aggregate and solids was dried in the 3-L beaker by means of the standard heating mantle used to heat the apparatus. The dried combined amount of aggregate and solids was weighed to calculate percent bitumen by difference.

An aggregate size distribution was determined (MDOT).

The solvent/extract and washings, totaling 4–5 L, were combined and distilled under an inert atmosphere of nitrogen gas (Carbon dioxide could be used.). The bitumen separated thus from the solvent was used to calculate percent bitumen directly and for a penetration test according to ASTM-D5 (conditions: 25 degrees C., 100 g needle, 5 second).

The following results were obtained.

| Lot | Sample wt. | Percent Bitumen | Percent Bitumen | R-Pen |
|-----|-----------|-----------------|-----------------|-------|
| A | 1,424.5 g | 5.7 (Difference) | 5.7 (Direct) | — |
| B | 1,453.8 g | 5.6 (Difference) | 5.5 (Direct) | 108 |
| C | 1,395.8 g | 5.8 (Difference) | 5.8 (Direct) | 87 |
| D | 1,038.3 g | 6.4 (Difference) | 6.0 (Direct) | 44 |
| E | 1,558.6 g | 7.1 (Difference) | 6.9 (Direct) | 79 |
| F | 1,483.1 g | 5.7 (Difference) | 5.6 (Direct) | 118 |

Thus, the percent bitumen results herefrom are quite comparable to those reported in the comparative data.

An examination of the recovered penetration values (R-Pen) indicates that bitumen extracts herefrom are significantly harder than those of the comparative data. This may be due to the high temperatures to which the bitumen was exposed during the extraction hereof since the maximum temperature encountered during the distillations of the cyclohexane was about the same as that encountered in distillation of the TCE to provide the comparative data, i.e., about 160–165 degrees D., even though a longer time was needed to remove the cyclohexane due to the larger quantity of it employed.

However, the validity of all of the recovered penetration values must be questioned because in most if not all of the distillations some light colorless oils of low volatility were observed separating from the bitumen before all of the cyclohexane had been removed to presumably leave the harder bitumen residue in the pot. Since the normal point of cyclohexane is 7 degrees C. below that of TCE and 6 degrees C. above that of 111-TCE, used by some testing laboratories, it would be difficult if not impossible to remove all of those chlorinated solvents without some oils separating also.

CONCLUSION

The present invention is thus provided. Numerous adaptations and modifications can be effected by those skilled in the art within the spirit of this invention, the asserted scope of which is particularly pointed out by the following distinctly claimed subject matter.

What is claimed is:

1. A procedure for bitumen extraction from an asphalt pavement sample comprising contacting the asphalt pavement sample with an alicyclic hydrocarbon solvent and under subcritical conditions at an extranormal temperature and pressure extracting bitumen values from the asphalt pavement sample thereby.

2. The procedure of claim 1, wherein the alicyclic hydrocarbon solvent is a cycloalkyl compound of four to twelve carbon atoms or mixture thereof.

3. The procedure of claim 2, wherein the extranormal percent of those temperatures within the range from the normal boiling point of the lowest boiling component of the solvent to the critical temperature of the solvent.

4. The procedure of claim 3, wherein the extranormal temperature is about from 75 to 90 percent of those temperatures within the range from the normal boiling point of the lowest boiling component of the solvent to the critical temperature of the solvent.

5. The procedure of claim 4, wherein the alicyclic hydrocarbon solvent is cyclopentane, cyclohexane, or a mixture thereof.

6. The procedure of claim 5, wherein the alicyclic hydrocarbon solvent is cyclohexane.

7. The procedure of claim 1, which is employs an apparatus comprising a housing section having imperforate walls, which is generally divided into lower and upper housing sections about a means for filtration, the lower housing section having imperforate lower and side walls and connectable to the upper housing section having imperforate side walls, the means for filtration being generally between interior volumes of the lower and upper housing sections, and an imperforate lid, useful for making a sealable bomb.

8. The procedure of claim 7, wherein the alicyclic hydrocarbon solvent is cyclopentane, cyclohexane, or a mixture thereof.

9. The procedure of claim 8, wherein the alicyclic hydrocarbon solvent is cyclohexane.

10. The procedure of claim 9, wherein a gradual cool down period is employed after subjection of the sample to the extranormal temperature and pressure.

* * * * *

UNITED STATES PATENT AND TRADEMARK OFFICE
CERTIFICATE OF CORRECTION

PATENT NO. : 5,053,118

DATED : Oct. 1, 1991

INVENTOR(S) : Thomas Houser

It is certified that error appears in the above-identified patent and that said Letters Patent is hereby corrected as shown below:

On the title page, in the ABSTRACT, l. 2, delete "bitument" insert -- bitumen --.

Col. 1, l. 22, insert a period after "test)."

Col. 1, l. 29, insert a period after "washings."

Col. 1, l. 53, insert a period after "performed."

Col. 1, l. 65, insert a period after "expensive."

Col. 2, l. 48, insert a period after "conditions."

Col. 2, l. 53, insert a period after "cyclohexane."

Col. 3, l. 43, delete "1982discloses" insert -- 1982), discloses --.

Col. 4, l. 35, after "alicyclic" insert the line:
-- hydrocarbon solvent under subcritical conditions and is --.

Col. 4, l. 52, insert a period after "objects."

Figure 4:
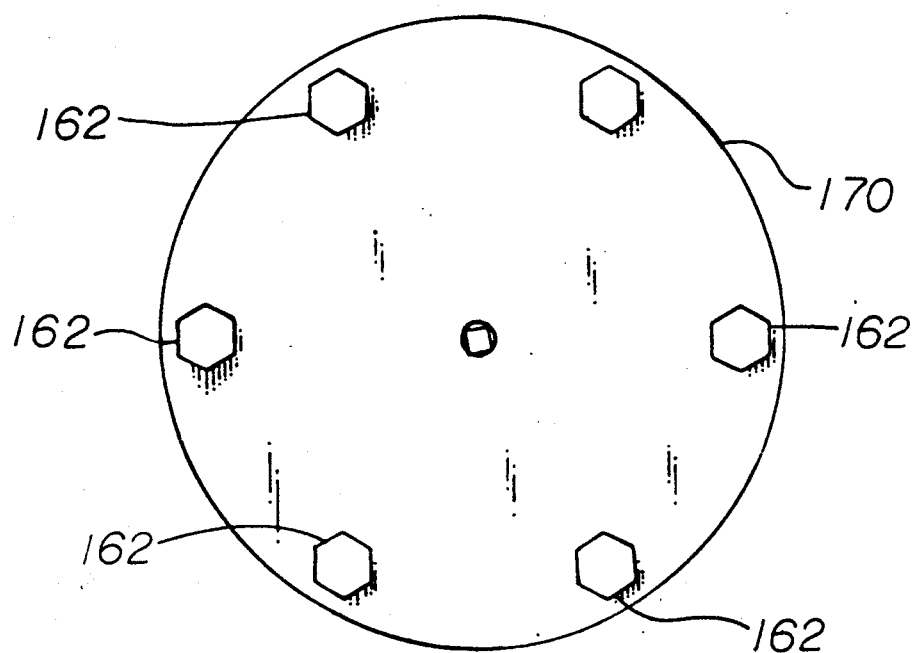

Col. 4, between ll. 63 & 64, insert the paragraph:
-- Figure 4 (Fig. 4) is a top view of the apparatus of Fig. 1. --.

Col. 5, l. 24, insert a period after "bitumen."

Col. 6, l. 15, insert a period after "hours."

UNITED STATES PATENT AND TRADEMARK OFFICE
CERTIFICATE OF CORRECTION

PATENT NO. : 5,053,118
DATED : Oct. 1, 1991
INVENTOR(S) : Thomas Houser

It is certified that error appears in the above-identified patent and that said Letters Patent is hereby corrected as shown below:

Col. 6, l. 27, insert a period after "desired."
Col. 6, l. 28, insert a period after "composition."
Col. 7, l. 26, insert a period after "2-359."
Col. 7, l. 54, insert a period after "pressure."
Col. 7, l. 65, delete "s" insert -- so --.
Col. 8, l. 10, after "e.g., the" insert the line:
-- lid, can be relatively cool without invalidating the --.
Col. 9, l. 13, delete "wit" insert -- with --.
Col. 9, l. 51, delete "D.," insert -- C., --.
Claim 3, l. 1 (col. 10, l. 25), after "extranormal" insert the line:
-- temperature is a temperature value of at least about 50 --.

Signed and Sealed this

Eleventh Day of August, 1992

Attest:

DOUGLAS B. COMER

Attesting Officer

Acting Commissioner of Patents and Trademarks